United States Patent
Efinger et al.

(10) Patent No.: US 8,133,175 B2
(45) Date of Patent: Mar. 13, 2012

(54) DEVICE FOR TEMPORARILY IMMOBILIZING TISSUE IN THE AREA OF A PULSATING BLOOD VESSEL

(75) Inventors: Andreas Efinger, Rietheim (DE); Rainer Hermle, Gosheim (DE)

(73) Assignee: Karl Storz GmbH & Co. KG (DE)

( * ) Notice: Subject to any disclaimer, the term of this patent is extended or adjusted under 35 U.S.C. 154(b) by 1383 days.

(21) Appl. No.: 11/693,808

(22) Filed: Mar. 30, 2007

(65) Prior Publication Data
US 2007/0232865 A1  Oct. 4, 2007

(30) Foreign Application Priority Data
Mar. 30, 2006  (DE) .......... 10 2006 016 003

(51) Int. Cl.
*A61B 1/32* (2006.01)
(52) U.S. Cl. ...................................................... 600/210
(58) Field of Classification Search .......... 600/201, 600/206, 208, 213–216, 218, 219
See application file for complete search history.

(56) References Cited

U.S. PATENT DOCUMENTS

| | | | |
|---|---|---|---|
| 5,749,892 A * | 5/1998 | Vierra et al. | 600/204 |
| 5,947,896 A * | 9/1999 | Sherts et al. | 600/229 |
| 6,036,641 A | 3/2000 | Taylor et al. | 600/231 |
| 6,074,375 A | 6/2000 | Stiles | 604/268 |
| 6,338,712 B2 * | 1/2002 | Spence et al. | 600/201 |
| 6,346,077 B1 * | 2/2002 | Taylor et al. | 600/204 |
| 6,383,134 B1 * | 5/2002 | Santilli | 600/205 |
| 7,338,441 B2 * | 3/2008 | Houser et al. | 600/206 |
| 2004/0082830 A1 | 4/2004 | Guenst et al. | 600/37 |
| 2006/0004250 A1 | 1/2006 | Parihar et al. | 600/37 |

FOREIGN PATENT DOCUMENTS

| | | |
|---|---|---|
| DE | 20 2004 012 637 U1 | 10/2004 |
| WO | WO 98/40018 | 9/1998 |
| WO | 00/15119 | 3/2000 |
| WO | 02/28287 | 4/2002 |

OTHER PUBLICATIONS

European Search Report, Jun. 28, 2007, 4 pages.

* cited by examiner

*Primary Examiner* — Anu Ramana
(74) *Attorney, Agent, or Firm* — St. Onge Steward Johnston & Reens LLC

(57) ABSTRACT

A device serves for temporarily immobilizing a tissue in an area of a pulsating blood vessel during a cardiac and thoracic surgical intervention. A pod of the device can be placed onto a tissue beneath a pulsating blood vessel. The pod has a rigid holder supporting a flexible element. The flexible element has suction openings in an area of contact with said tissue. The pod has a connector piece for the connecting to an underpressure source. A flexibility of said flexible element is in that said flexible element adapts to a shape of said tissue in said area of contact when placed on said tissue.

9 Claims, 5 Drawing Sheets

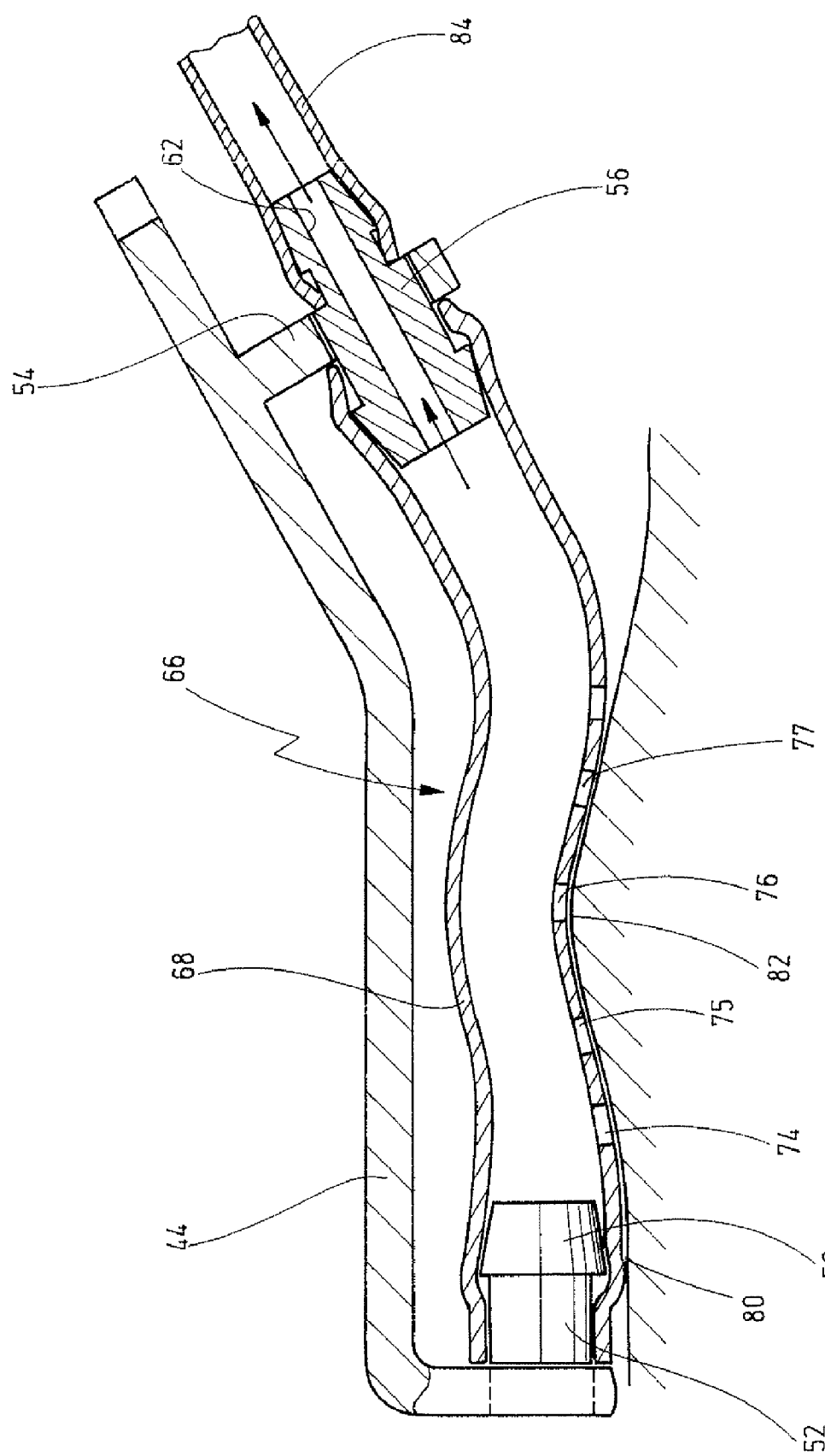

DEVICE FOR TEMPORARILY IMMOBILIZING TISSUE IN THE AREA OF A PULSATING BLOOD VESSEL

BACKGROUND OF THE INVENTION

The invention relates to a device for temporarily immobilizing tissue in the area of a pulsating blood vessel, in particular a coronary vessel, during a cardiac and/or thoracic surgical intervention.

A device of this kind is known from WO 02/28287 A1, for example.

Such devices are used in cardiac and/or thoracic surgical interventions in which procedures are carried out on the coronary vessels of a beating heart. One of these techniques is called the MIDCAB (minimally invasive direct coronary artery bypass) technique. This technique is performed through an intercostal space.

In another operating technique, the sternum is cut through along its length, and the thoracic cage is spread open sideways using rib retractors. To permit better access to the heart, one half of the thoracic cage, namely the left half, is lifted relative to the right half of the thoracic cage. Procedures can now be carried out on the beating heart without the heart having to be connected to a heart-lung machine, referred to as OPCAB (off-pump coronary artery bypass) procedures.

In procedures carried out on the beating heart, a sternal artery, for example, which has been suitably prepared in advance, is sutured directly onto a vessel of the beating heart in order in this way to create a bypass round a coronary vessel stenosis or occlusion. Since, as has already been mentioned, the heart is still beating, how-ever, that is to say making pulsating movements, it is very difficult to perform a procedure at this site.

In order to immobilize or stabilize the tissue in the area of the vessel where the bypass is to be created, the aforementioned devices, which are also called OPCAB stabilizers, have become established.

Devices of this kind comprise a pod which can be placed onto adjacent tissue on both sides of and alongside the vessel of the beating heart and which thus immobilizes this area.

Depending on its design, the pod is in the shape of a fork head with two approximately parallel prongs that can be placed on both sides of the vessel, or, as in the publication mentioned at the outset, it is made up of two individual structural parts which can each be placed onto one respective side of the vessel. The pod, or the prong, is connected to an arm, the latter in turn being connected to a stationary apparatus, for example mounted on an aforementioned rib retractor. In this way, the pod can be placed with a certain pressure onto the tissue and immobilizes the latter in the area to the left and right of the vessel on which the procedure has to be carried out.

The pod is provided with suction openings via which the tissue can additionally be sucked onto the pod by an underpressure, such that it is almost impossible for pulsating movements to take place in this area, and the operating surgeon thus has access to a substantially stationary, i.e. immobilized, operating site.

Since interventions of this kind are performed on one of the most important of the vital organs, the beating heart, whose function has greatly deteriorated as a result of pathological changes, it is desirable to be able to adapt the pod as effectively as possible to the anatomical anomalies in the contact area.

Therefore, in aforementioned document WO 02/28287 A1, and particularly in WO 00/15119 A2, numerous adjustment possibilities are provided in the area of the pod, such that the latter can be adjusted with as many degrees of freedom as possible. These include twisting, tilting and pivoting of the pod, or of the two prongs relative to one another. In this way, it is possible to permit adaptation to certain orientations of the tissue. In the final analysis, however, the tissue always has to adapt to the pod, which is made of rigid materials.

WO 00/15119 A2 mentions at one point that the entire pod can be produced from a plastically deformable material, such that it can be bent in situ into a defined orientation by the operating surgeon. However, in this case too, the tissue then has to adapt to this bent pod, for example one that has been bent in steps.

U.S. Pat. No. 6,074,375 discloses a device for introducing a liquid into the heart muscle. The liquid is introduced into the muscle of the beating heart with a kind of syringe. In order to immobilize the tissue area at the injection site, a two-legged suction pod is provided which can be placed onto the heart muscle and through which a vacuum can be established. Suction openings at the outer end of the two legs serve to suction the tissue. The legs have flexible portions in order to adapt them to the contour of the heart surface. The legs remain in the bent orientation. A soft elastic layer serves as a seal between the muscle surface and the outer end with the suction openings. Here too, the tissue adapts to the shape of the pod.

German Utility Model DE 20 2004 012 637 U1 discloses a suction stabilizer having a basic body onto which a suction rail can be mounted. The suction rail is made of a relatively hard material.

It is, therefore, object of the present invention to make available a device of the type mentioned at the outset which permits less traumatic immobilization of the tissue.

SUMMARY OF THE INVENTION

According to the invention, the object is achieved by the fact that the device for temporarily immobilizing a tissue in an area of a pulsating blood vessel comprises a pod which can be placed onto a tissue beneath a pulsating blood vessel, said pod having a rigid holder supporting a flexible element, said flexible element having suction openings in an area of contact with said tissue, said pod having a connector piece for the connecting to an underpressure source, wherein the flexibility of said flexible element is in that said flexible element adapts to a shape of said tissue in said area of contact when placed on said tissue.

The design now proposed here makes it possible, on the one hand, to achieve, via the rigid holder, a precisely defined spatial orientation of the pod relative to the tissue, which orientation is spatially fixed and also ensures that a certain contact pressure can be exerted. By provision of the flexible element in the contact area, it is possible, on the other hand, for the pod to adapt to a certain extent to the shape of the tissue in the contact area in the region of the flexible element, and not the other way round. If, for example, a tissue eminence is present in the contact area, it is able to press into the flexible element, such that the contour of the flexible element adapts to the contour of the tissue in the contact area. Since the suction openings are present in the flexible element, the suction openings settle exactly onto the tissue area, for example even on curved areas or on the aforementioned eminence. If an underpressure is now applied to the suction openings, the tissue lying in the contact area is suctioned purely for additional retention, and it is no longer deformed or altered in its entirety. This allows to exert only a slight underpressure.

To put it another way, if a rigid rectilinear holder were to be placed, for example, onto a tissue area with the aforementioned eminence, the eminence would have to be pressed into the depths of the tissue. If this is to be avoided, the tissue which after all lies closer to the contact area in the area of the eminence, would be suctioned more than in other areas, i.e. a relatively strong deformation would take place in these areas upon application of the underpressure.

This could, for example, lead to a situation where the operating surgeon, initially without applying the underpressure, has placed the pod onto the tissue in what he believes to be a very good orientation, only to find, after application of the underpressure, that undesired changes in position or shifting of the tissue can then take place.

This can be largely avoided using the design with the flexible element, by virtue of the fact that the flexible element adapts to the tissue in the contact area, with the flexible element being able to settle itself onto the tissue. The underpressure applied through the suction openings in the flexible element then no longer leads to substantial tissue movements, but only to an additional adherence of the tissue to the pod. It is thus possible to achieve particularly atraumatic placement and immobilization of the tissue, for example on the beating heart.

In another embodiment of the invention, the flexible element is mounted releasably on the holder.

This measure has the advantage that elements of different flexibility can be applied depending on the anatomical circumstances at the operating site.

In another embodiment of the invention, the holder is made of metal material.

This measure has the advantage, particularly with the design with releasable mounting of the flexible element, that the holder is suitable for repeated use, that is to say can be suitably cleaned and sterilized after the flexible element has been removed following an intervention.

To this end, in a further embodiment, provision is made for the flexible element to be designed as a disposable part for one-off use.

This measure has the advantage that, after an operation has been performed, the flexible element is removed and discarded. In this state, that is to say without the flexible element, the arm can be cleaned and sterilized, and a new flexible element is attached for the next intervention.

In another embodiment of the invention, the flexible element is designed as a tubular element.

This measure has the advantage that the tube geometry, with selection of suitable dimensions and materials, permits great variability in terms of the degree of flexibility of the element. At the same time, an underpressure can be applied via the tubular element in order to achieve the additional fixing of the tissue on the tubular element. The geometry of a tubus allows with flexible materials also to maintain the tubular geometry if a certain underpressure is exerted within the tubus without collapsing it.

In another embodiment of the invention, the tubular element can be connected at one end to a suction connector piece of the holder.

This measure has the advantage that the aforementioned application of an underpressure is easy to do, namely by means of the tubular element being pushed onto a corresponding suction connector piece of the holder.

In another embodiment of the invention, the flexible element in the contact area comes to lie at a distance from a body of the holder.

This measure has the advantage that the flexible element can move or bulge out towards the sides, for example to be able to adapt to extreme curvatures or other anomalies in the area of the tissue. However, the fact that the flexible element is mounted on a rigid holder limits this yield, with the result that the desired contact pressure can be exerted.

In another embodiment of the invention, the holder is designed as a strip from whose side facing the tissue at least one retaining element protrudes onto which the flexible element can be mounted.

This measure has the advantage that, on the contact side of the strip, quite a lot of space is available for provision of the retaining devices for the flexible element, onto which devices the flexible element can be mounted either releasably or non-releasably, depending on the particular design.

In another embodiment of the invention, the tubular element is designed as a tube piece which at one end can be pushed onto a suction connector piece and at the other end can be pushed onto a retaining plug.

This measure has the advantage that the tubular element is particularly inexpensive to produce, is particularly easy to handle and, because of its geometry, permits particularly atraumatic application.

The corresponding tube piece, which is kept in stock either as a length with predetermined break points or as an individual piece, simply needs to be pushed onto the two connector pieces such that the device is ready for use.

In another embodiment of the invention, the pod is designed as a fork head with two prongs, each prong being designed as a rigid holder with a flexible element mounted on it.

This measure has the advantage that, as a single element, the pod can be applied in one step on both sides of the vessel to be immobilized, and the pod is equipped on both sides with a flexible element, such that the whole pod can be applied onto the tissue in a particularly atraumatic manner.

In another embodiment of the invention, the suction openings are provided in the jacket of the tube piece.

This measure has the advantage that this can be done very easily by machine, and the tube piece is available as a prefabricated replacement part, if appropriate in a sterile package.

In another embodiment of the invention, the pod is mounted on an arm which can bend in all spatial directions and can be fixed in these bend positions.

This measure known per se has the advantage that, by way of the arm, the operating surgeon can place the pod in a position which is ergonomically suitable for him and easily accessible for the operation, and the pod can then be fixed in this position.

In another embodiment of the invention, the arm, at the end remote from the pod, is provided with a support fixture via which the arm can be secured on a retractor.

This measure has the advantage that the device can be mounted on a structural part that is present anyway in the operation, namely the rib retractor that spreads open the thoracic cage. This structural part is relatively fixed in its position and serves as an abutment for the arm, such that the operating surgeon can very easily bring the pod into a defined position in which it is spatially and positionally fixed relative to the retractor, with the pod then coming to lie on the tissue.

It will be appreciated that the aforementioned features and those still to be explained below can be used not only in the respectively cited combination, but also in other combinations or singly, without departing from the scope of the present invention.

BRIEF DESCRIPTION OF THE DRAWINGS

The invention is described and explained in more detail below on the basis of a selected illustrative embodiment and with reference to the attached drawings, in which:

FIG. 5 shows a cross section similar to FIG. 4, showing the adaption of the flexible element to the contour of the tissue.

Figure 1:
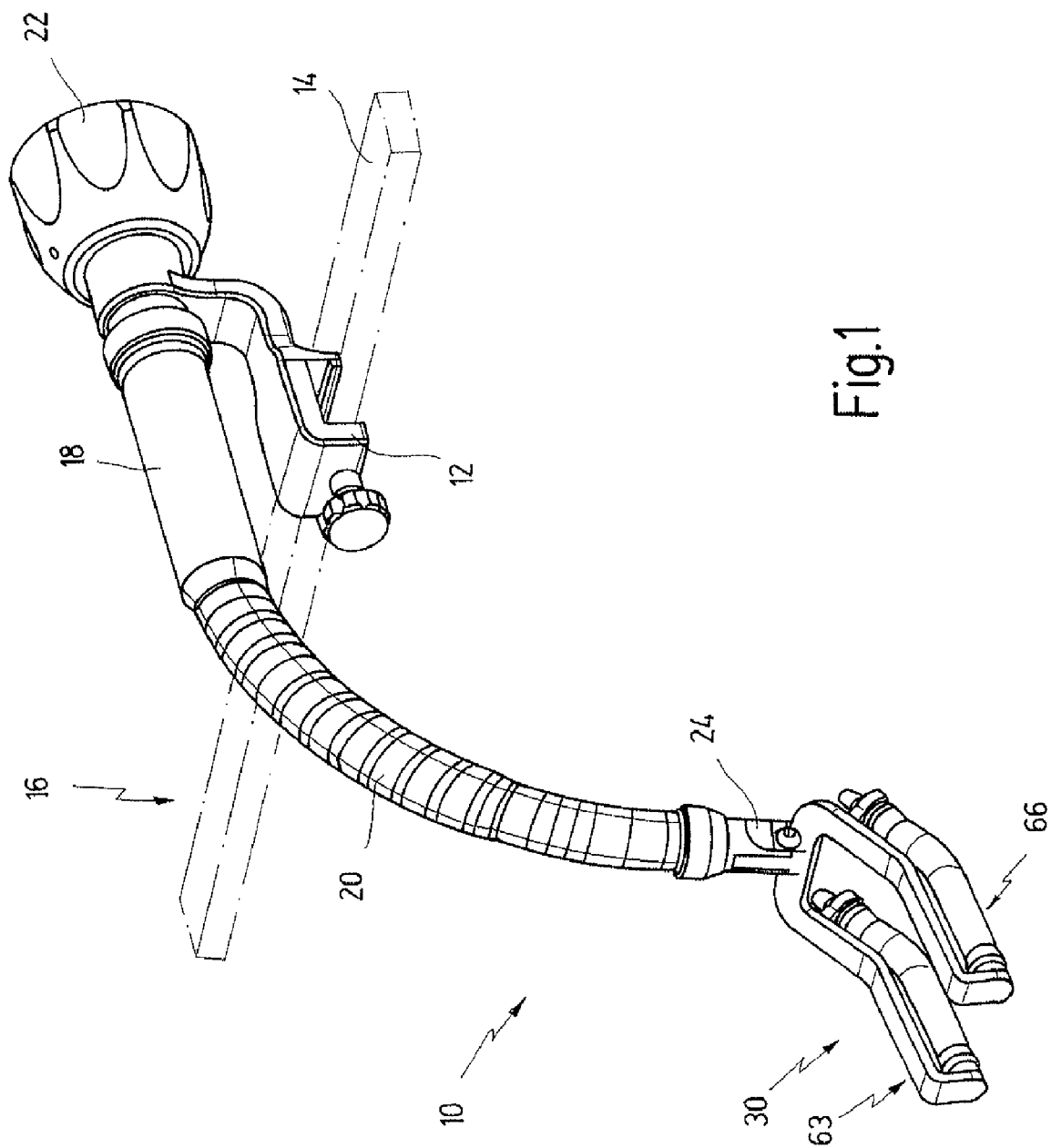
FIG. 1 shows a perspective view of a device according to the invention, which is mounted on a rail of a retractor.

A device according to the invention shown in FIGS. 1 to 5 is designated in its entirety by reference number 10.

The device 10 has, at one end, a support fixture 12 via which the device 10 can be mounted onto a rail 14 of a rib retractor 16.

In this design, the device 10 is thus a functional element of a retractor.

An arm 18, which is designed as a so-called Leyla arm 20, extends from the support fixture 12. Such a Leyla arm 20 is characterized by the fact that it can be bent in all spatial directions and can be locked in such a bent position. For this purpose, such a Leyla arm 20 is composed of individual hinge-like elements that permit this bending. To lock it, a pulling wire extends through the center of the arm and is connected to an adjusting knob 22. As has been mentioned, the arm 18 can be moved in all spatial directions when the adjusting knob 22 is loosened. By tightening the adjusting knob, the arm remains locked, for example in the bent position shown in FIG. 1.

At its end remote from the adjusting knob 22, the arm is connected to a pod 30 via a hinge 24.

The pod 30 is designed as a fork head 32 with two parallel prongs 34 and 36 which are connected to one another via a crosspiece 38. The fork head 32 is produced from a strip 40 of metal material.

Starting from the crosspiece 38, each of the two prongs 34 and 36 has a first portion 42, which merges via a bend into a second portion 44, the outer end of which merges approximately at a right angle into a bent end portion 46.

Figure 2:
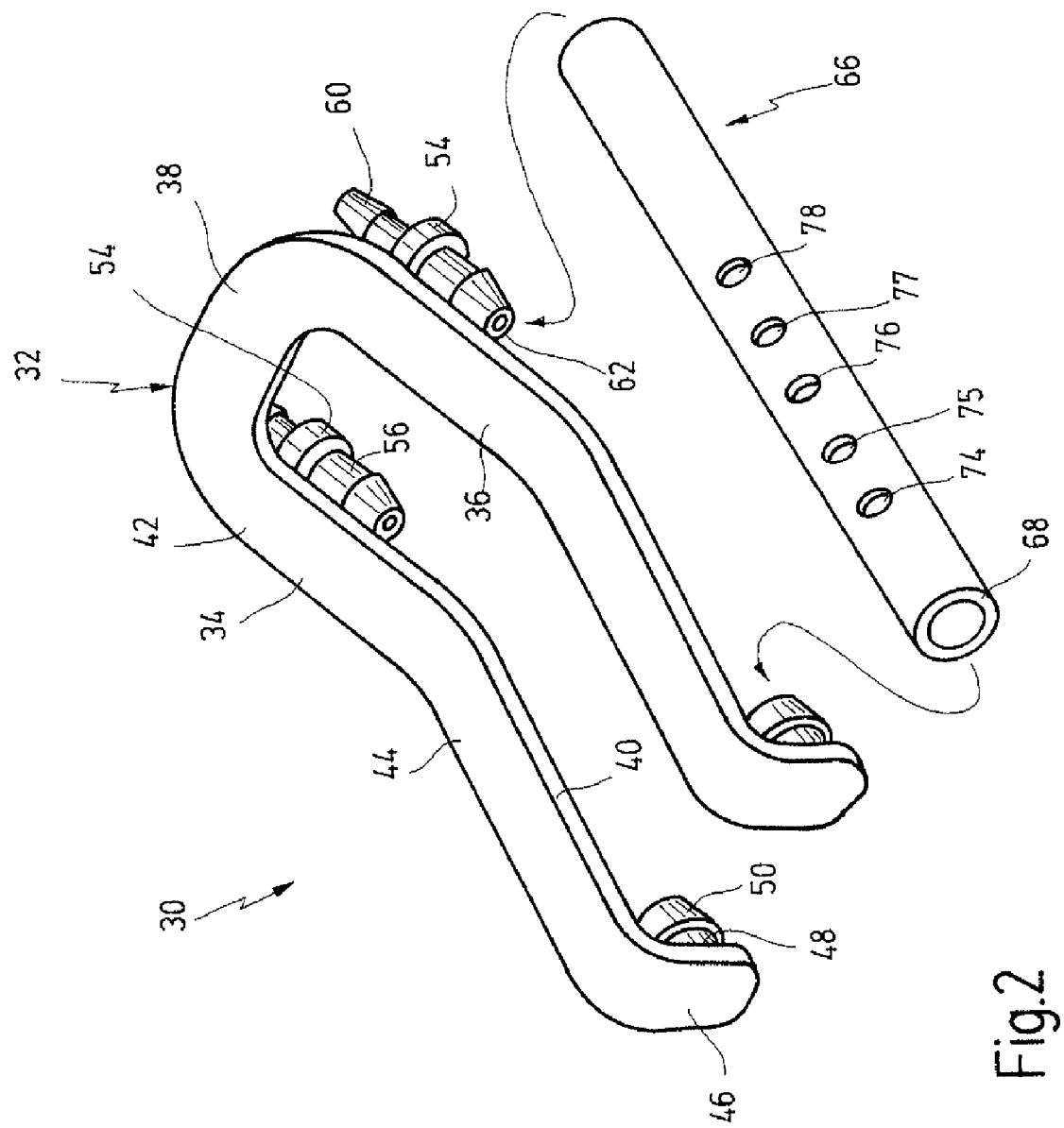
FIG. 2 shows a perspective detail of a pod of the device from FIG. 1 in an partially exploded view, that is to say with the flexible element not yet attached, or with the flexible element having been removed.
Figure 3:
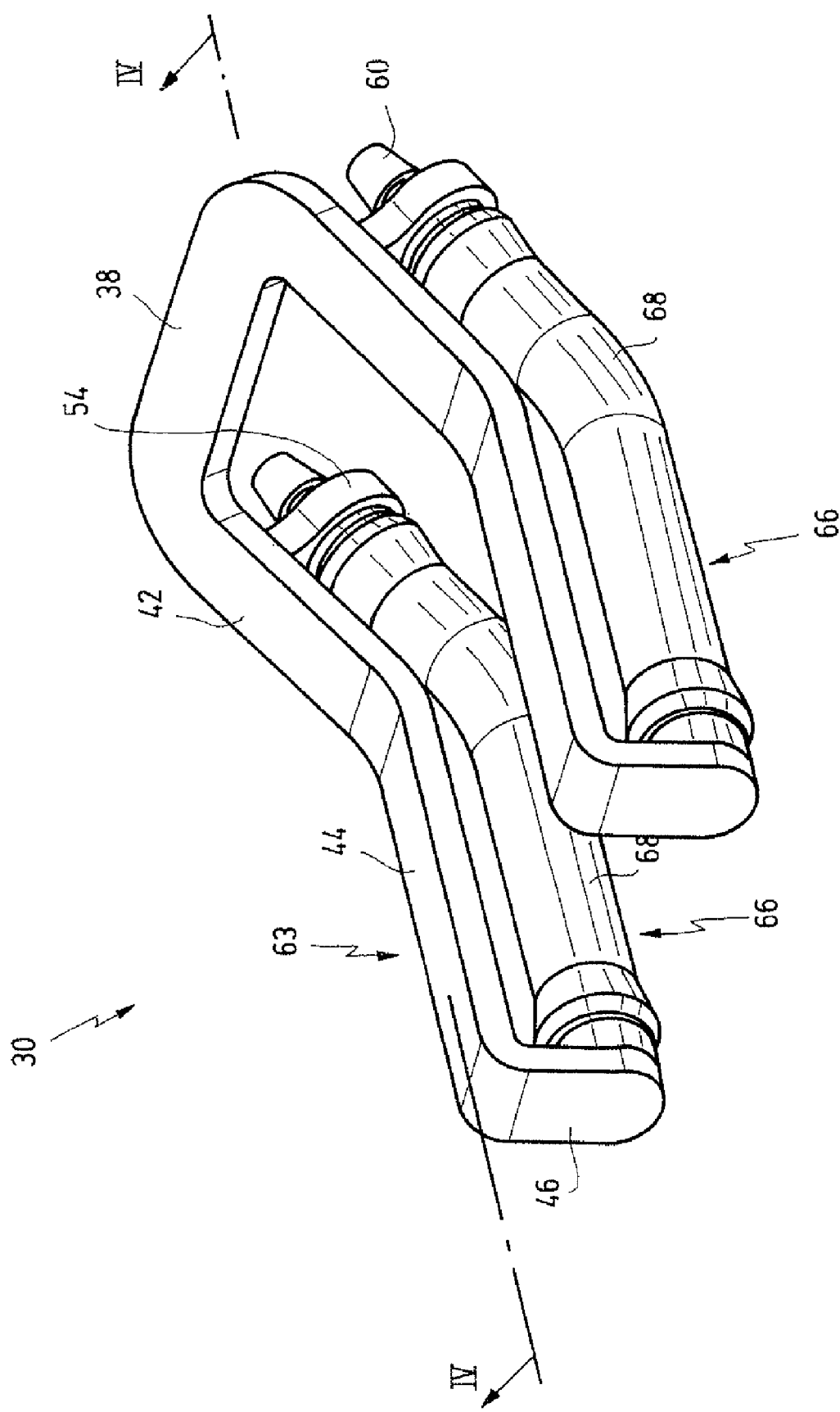
FIG. 3 shows a greatly enlarged perspective detail of the pod from FIG. 1.
Figure 4:
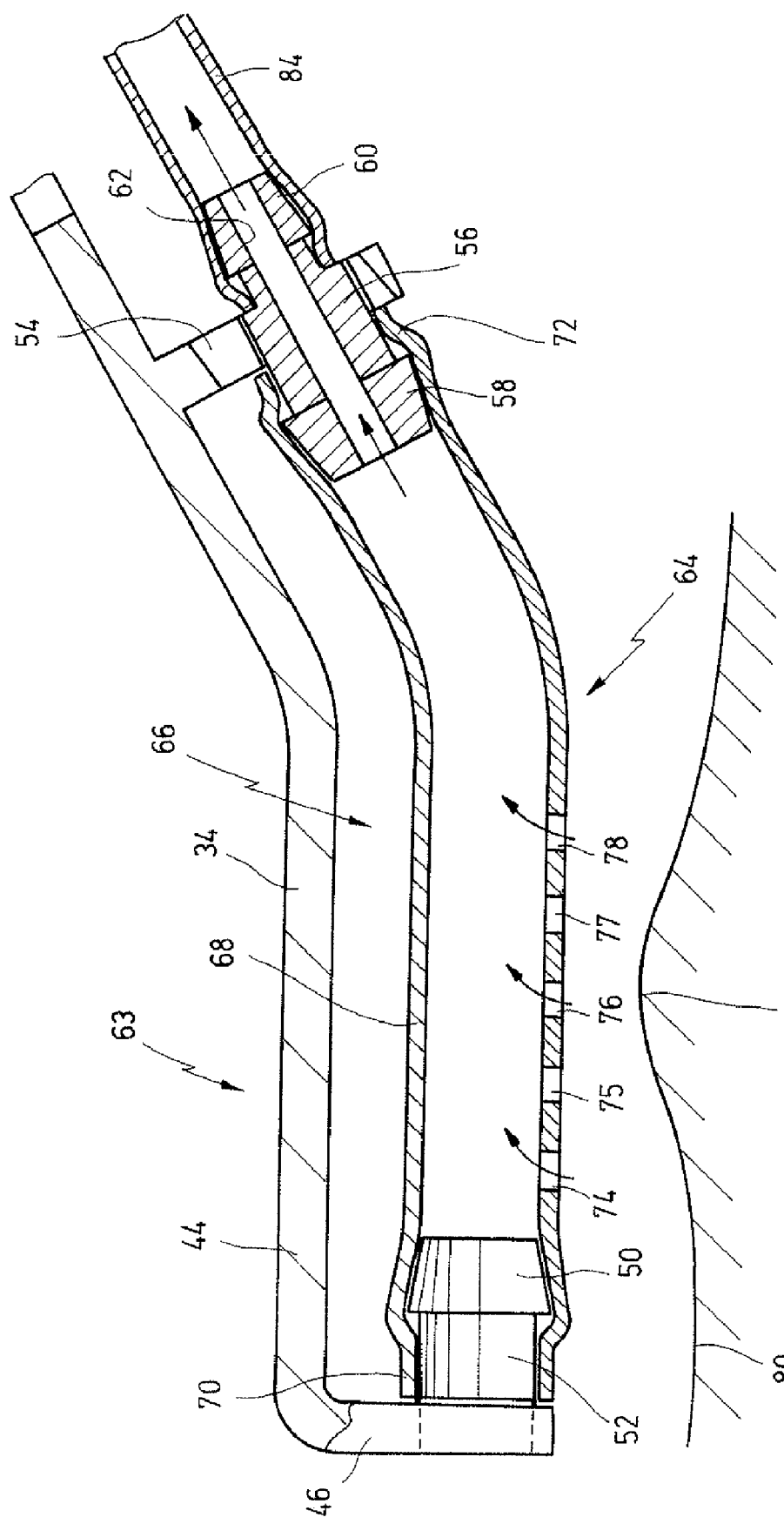
FIG. 4 shows a cross section along the line IV-IV in FIG. 3, with attached vacuum line.

A conical plug 50 protrudes from the inner face 48 of the bent portion 46 (see in particular FIGS. 2 and 4).

The conical plug 50 has a neck 52 which is received in an opening (not shown here) in the bent portion 46.

In the area after the crosspiece 38, an eyelet 54 into which a suction connector piece 56 is mounted extends in each case from the underside of each prong 34 and 36.

The suction connector piece 56 has a first connector piece 58 which extends conically and which is directed towards the conical plug 50.

A second connector piece 60 extends from the opposite side of the eyelet 54. A suction channel 62 extends centrally through the suction connector piece 56.

A flexible element 66 in the form of a tube piece 68 can be pushed onto the conical plug 50 at one end and onto the first connector piece 58 at the other end.

As can be seen from FIG. 4, hose piece 68 lies at a distance to the body of the holder 63, allowing the hose piece 68 in an area of contact with a tissue 80 to bend or to curve laterally, as can be seen in FIG. 5.

It will be seen from the cross-sectional view in FIG. 4 that one end 70 of the tube piece 68 is pushed completely over the conical plug 50 and over the latter's neck 52 and is therefore received there with a secure fit.

It will be seen from the cross-sectional view in FIG. 4 that the transition from the conical plug 50 to the cylindrical neck 52 forms an undercut over which the end 70 of the tube piece 68 has to be pushed, and which thus prevents the tube piece 68 from coming off.

The same applies for the opposite end 72 of the tube piece 68. This is pushed onto the first connector piece 58 of the suction connector piece 56, again in a captive manner.

It will be seen in particular from the cross-sectional view in FIG. 4 that each of the prongs 34 and 36 is designed, in conjunction with the conical plug 50 and the first connector piece 58, as a rigid holder 63, which serves as holder for the flexible element 66.

The tube piece 68 is composed of a silicone tube in whose wall five suction openings 74 to 78 are cut out on one side (see in particular FIG. 2).

The tube piece 68 is chosen such that it has a flexibility in the portion between the plug 50 and the connector piece 58, but is nevertheless still dimensionally stable, such that it does not collapse when an underpressure is established inside the tube piece 68.

As can be seen from FIG. 5, a vacuum line 84 connected to an underpressure source is pushed onto the second connector piece 60.

In practical implementation, the device 10 is, for example, applied to a coronary vessel such that a section of this vessel extends parallel to and between the two prongs 34 and 36. For this purpose, the device 10, or its pod 30, in a contact area 64 extending along the length of the tube piece 68, is placed onto a corresponding tissue 80 on both sides of the blood vessel between the prongs 34 and 36.

If, for example, an eminence 82 is present in this area, the flexibility of the tube piece 68 allows the flexible element 66 to adapt to the curvature of the eminence 82 to a certain extent. In this way, the five suction openings 74, 75, 76, 77 and 78 then also settle uniformly onto the tissue 80. It will be seen from FIG. 4 that the eminence 82 will initially only come into contact with the suction opening 76. The suction openings 75 and 77 to either side would still be at a certain distance from the tissue 80, and the suction openings 74 and 78 at the ends would still be at a considerable distance from it.

Due to the particular flexibility of the flexible tube piece 68 it can adapt to the geometry of the tissue 80 and settle on the latter atraumatically, as can be seen best from FIG. 5.

However, by means of the rigid holder 63, a sufficient contact pressure can still be exerted by the tube piece 68 in order to immobilize the tissue 80 in this area.

By applying an underpressure via the vacuum line 84, the tissue 80 can additionally be fixed on the tube piece 68 and thus also further immobilized at the same time, again atraumatically, since the tube areas with the suction openings 74 to 78 have already settled onto the tissue 80.

After the intervention, the tube piece 68 simply needs to be detached from the plug 50 and from the connector piece 58 and can be discarded, such that the pod 30 or its metal components can be cleaned and sterilized.

For a subsequent intervention, a new tube piece 68 is then mounted onto the underside of each prong 34 and 36, such that the device 10 is ready for a new intervention.

The invention claimed is:

1. A device for temporarily immobilizing a tissue in an area of a pulsating blood vessel during a cardiac and thoracic surgical intervention, comprising
a pod which can be placed onto a tissue beneath a pulsating blood vessel,
said pod having a rigid holder supporting a flexible element, said flexible element having suction openings in an area of contact with said tissue, said pod having a connector piece for connecting to a suction source,
wherein a flexibility of said flexible element is in that said flexible element adapts to a shape of said tissue in said area of contact when placed on said tissue;
wherein said holder has a body designed as a strip, said strip having a side facing said tissue, at least one retaining plug protrudes from said side, said at least one retaining plug configured to receive said flexible element,
wherein said flexible element is designed as a tube piece which at one end is pushed onto said connector piece and at the other end is pushed onto said at least one retaining plug of said strip.

2. The device of to claim 1, wherein said flexible element is mounted releasably on said holder.

3. The device of claim 1, wherein said holder is made of a metal material.

4. The device of claim 1, wherein said flexible element is designed as a disposable part for single use.

5. The device of claim 1, wherein said tube piece is located at a distance from a body of said holder.

6. The device of claim 1, wherein said pod has a fork head with two prongs, each prong being designed as a rigid holder with said tube piece mounted on it.

7. The device of claim 1, wherein said suction openings are provided in a wall of said tube piece.

8. The device of claim 1, wherein said pod is mounted on an arm which can be bent in all spatial directions and can be fixed in these bent positions.

9. The device of claim 8, wherein said arm, at an end remote from said pod is provided with a support fixture via which said arm can be secured on a retractor.

\* \* \* \* \*